(12) United States Patent
Kelly

(10) Patent No.: US 8,118,739 B2
(45) Date of Patent: Feb. 21, 2012

(54) ENDONASAL SPECULUM

(75) Inventor: Daniel F. Kelly, Pacific Palisades, CA (US)

(73) Assignee: Mizuho America, Union City, CA (US)

( * ) Notice: Subject to any disclaimer, the term of this patent is extended or adjusted under 35 U.S.C. 154(b) by 983 days.

(21) Appl. No.: 12/009,948

(22) Filed: Jan. 23, 2008

(65) Prior Publication Data

US 2009/0187081 A1    Jul. 23, 2009

(51) Int. Cl.
*A61B 1/32* (2006.01)
(52) U.S. Cl. ...................................................... 600/235
(58) Field of Classification Search .................. 600/199, 600/201–246; 606/199
See application file for complete search history.

(56) References Cited

U.S. PATENT DOCUMENTS

| | | | | |
|---|---|---|---|---|
| 730,284 | A * | 6/1903 | Monosmith | 600/219 |
| 3,664,330 | A * | 5/1972 | Deutsch | 600/104 |
| 4,576,168 | A * | 3/1986 | Jalowayski | 606/198 |
| 5,772,582 | A * | 6/1998 | Huttner et al. | 600/219 |
| 5,931,777 | A * | 8/1999 | Sava | 600/213 |
| 6,102,852 | A * | 8/2000 | Liu | 600/219 |
| 6,224,546 | B1 * | 5/2001 | Ramadan | 600/235 |
| 6,302,842 | B1 * | 10/2001 | Auerbach et al. | 600/220 |
| 6,702,741 | B2 * | 3/2004 | Rioux et al. | 600/233 |
| 6,869,398 | B2 * | 3/2005 | Obenchain et al. | 600/224 |
| 7,481,766 | B2 * | 1/2009 | Lee et al. | 600/214 |
| 7,631,981 | B2 * | 12/2009 | Miller et al. | 362/119 |
| 2002/0133060 | A1 * | 9/2002 | Doyle | 600/210 |
| 2003/0055320 | A1 * | 3/2003 | McBride et al. | 600/217 |
| 2004/0024291 | A1 * | 2/2004 | Zinkel | 600/218 |
| 2005/0080320 | A1 * | 4/2005 | Lee et al. | 600/214 |

OTHER PUBLICATIONS

K. Arita et al. "Transsphenoidal Cross Court Approach Using a Slightly Modified Speculum to Reach Pituitary Adenomas with Lateral Growth".
J. Hardy et al. "Forces Applied by Nasal Speculums during Transsphenoidal Operations".
E. Kern et al. "A speculum for transseptal, transsphenoidal pituitary surgery".
M. Kitano et al. "An adjustable nasal speculum for the extended transsphenoidal approach".
A. Landolt "Modification of the Cushing speculum used for transsphenoidal pituitary surgery".
H. Miyake "Modification of a nasal speculum for transsphenoidal surgery".
N. Nakao "A Minimally Invasive Endoscopic Transsphenoidal Approach with an Endonasal Septal Pushover Technique by Using a Modified Nasal Speculum".

* cited by examiner

*Primary Examiner* — Thomas C. Barrett
*Assistant Examiner* — Christopher Beccia
(74) *Attorney, Agent, or Firm* — Robert Schuler

(57) ABSTRACT

A short (60-70 mm) endonasal speculum for performing operations within and around the sellar region of the human head includes two side members each of which is composed of a handle and an elongated blade. The handles are attached to each other by a hinge and one of the handles includes a variable dilation control that is used to open the speculum. The elongated blades are arcuate in cross section and have distal ends that are opposed to each other in a trapezoidal configuration, either up or down, which permits greater visualization and access into the regions above and below the sella and greater instrument maneuverability within the speculum.

9 Claims, 5 Drawing Sheets

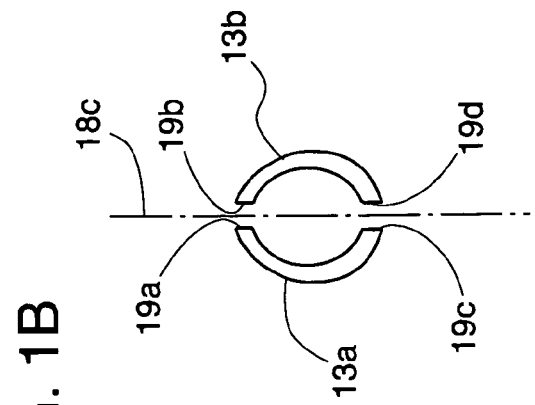
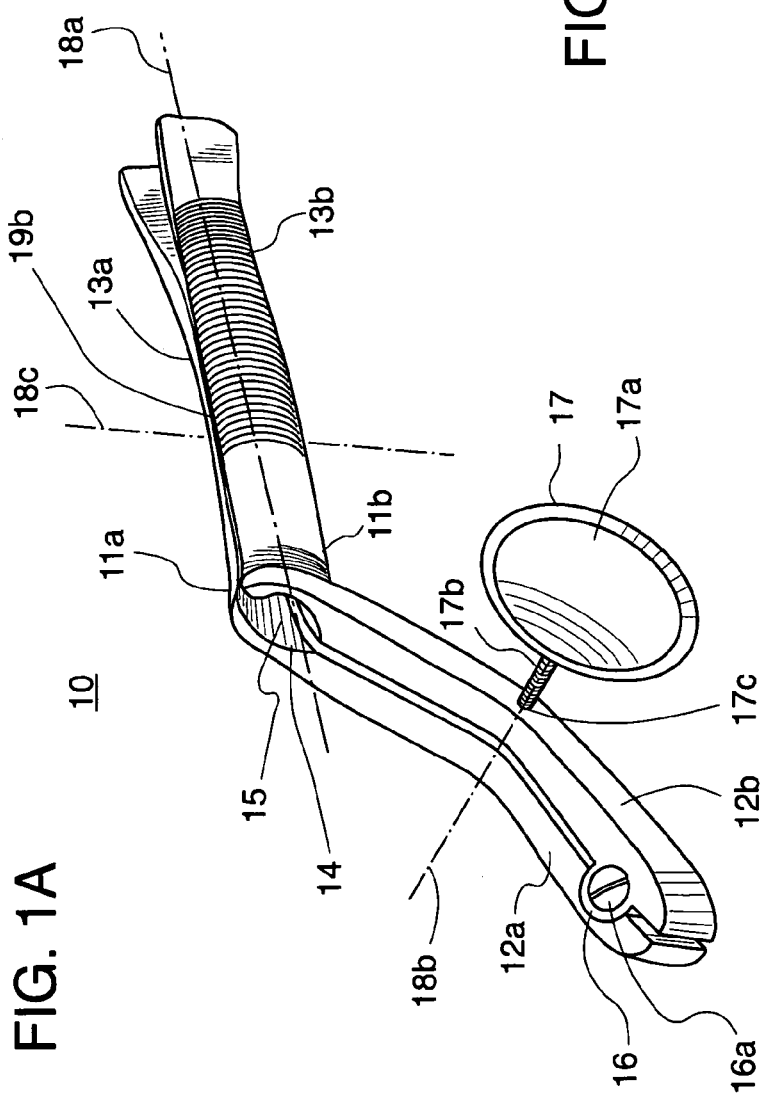
FIG. 1A
FIG. 1B

ENDONASAL SPECULUM

FIELD OF THE INVENTION

The invention relates generally to the area of endonasal surgical instrumentation and specifically to a surgical instrument suitable for transsphenoidal surgery performed through the endonasal corridor.

BACKGROUND OF THE INVENTION

Surgical instruments have been designed in order to provide minimally invasive visual and physical access to certain areas within the human head, such as the suprasellar, parasellar and cavernous sinus areas. With the introduction of rhinoscopy in the mid-19$^{th}$ century, a variety of specula were designed for transnasal surgery. An early speculum designed by Fraenkel combining fenestrated blades with a self-retaining screw arrangement was employed for the first transseptal modification of the transnasal pituitary operation. The fenestrated blades permit a surgical instrument, such as a cutting device, to be inserted through the speculum in order to make incisions into the sphenoidal sinus for instance. In 1914, Cushing designed a speculum whose dimensions allowed improved visualization of the sella floor using a sublabial approach. Later, when the use of surgical microscopes became prevalent, Hardy solved the problem of the speculum's tendency to slip backward by adding toothed edges to the inferior blade surface. A 1975 technical note authored by Landolt and Novoselac, describes a modification to the Cushing speculum in which the distal ends of a speculums blades are bent outward to retain the tissue outside the surgical field. In 1980, Laws and Kern developed a modification of the Hubbard speculum that included a self-retaining retractor and distally flanged concave blades which both frees the surgeon's hands and enhances lateral exposure in the area of interest. More recently, additional modifications to transsphenoidal speculums have been introduced to laterally expand visualization within the sellar area. These changes include thinning the proximal ends of the speculum blades, shortening of one speculum blade for better contralateral exposure and adding an additional hinge to provide a wider surgical field.

Currently available endonasal speculums typically have elongated blades that are curved in cross section from their proximal to distal ends which result in an oval-shaped surgical corridor. Although, the current speculum blade design provides adequate exposure for sellar targets situated directly in-line with the speculum, in many instances the target extends beyond the sellar region either superiorly in the suprasellar space or inferiorly in the clival region. In the event that the target extends beyond the sellar region, inadequate exposure is often encountered if one is trying to access suprasellar tumors such as craniopharyngiomas, tuberculum sella meningiomas or adenomas with large suprasellar extensions. Similarly, access to infrasellar lesions such as clival chordomas or prepontine epidermoid tumors are limited by the curved speculum blade construction. The long tubular construct of the speculum, which is typically 70 to 90 mm in length, further restricts parasellar visualization, which becomes more problematic as the speculum length increases.

SUMMARY OF THE INVENTION

A novel short (60-70 mm) endonasal speculum design extends the surgical field, permitting better superior and inferior visualization and surgical instrumentation access to the suprasellar space and the clival region of the human head. The novel endonasal speculum design results in improved visibility and access in a blade design where the distal ends of the blades are linear in cross section and opposed to each other at an angle that both permits improved access to the target either in the area above the sella (trapezoidal-up speculum) or in the area below the sella (trapezoidal-down speculum). This design and shorter working length of the speculum yields a larger cross-sectional area of exposure in the surgical field and greater instrument maneuverability within the speculum itself because the traditional distal curved (oval) blade design has been eliminated.

In one embodiment, an endonasal speculum is comprised of two substantially bilaterally symmetrical side members each of which have a proximal and a distal end and include a variable dilation control mechanism; each of the two side members include a handle and each of the handles are joined to a substantially straight elongated blade each of which has a proximal and distal end; an aperture is formed at the junction of the handles and the blades; the blades transition from an arcuate cross section at the junction with the handles to a linear cross section at the distal ends; and the distal ends of the blades are opposed to each other in cross section at a specified angle.

In another embodiment, the distal ends of the blades are opposed to each other in cross section in a trapezoidal-up angle in which the distal ends flare outward away from each other from inferior to superior.

In another embodiment, the distal ends of the blades are opposed to each other in cross section in a trapezoidal-down angle in which the distal ends flare outward away from each other from superior to inferior.

BRIEF DESCRIPTION OF THE DRAWINGS

FIG. 1A is a perspective view of the endonasal speculum.
FIG. 1B is a cross sectional view of the proximal ends of the speculum blades.

DETAILED DESCRIPTION OF THE INVENTION

Figure 1D:
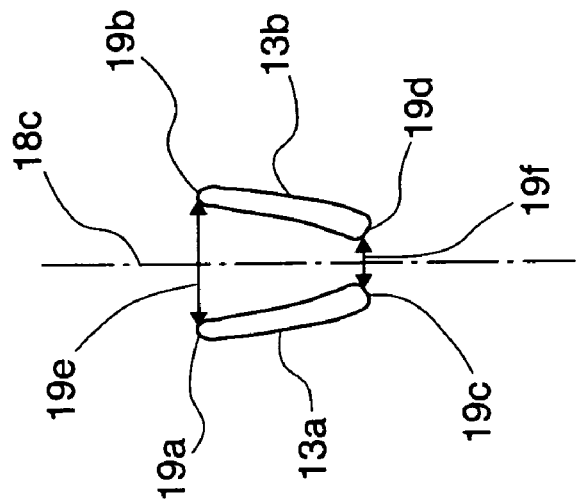
FIG. 1D is a cross sectional view of the distal ends of the speculum blades.

An endonasal speculum 10 in FIG. 1A is employed in the transsphenoidal approach to expose and provide access by surgical instruments to suprasellar and infrasellar lesions. Endonasal speculum 10 generally includes a first side member 11a, a second side member 11b and each of the side members 11a and 11b are preferably fabricated from a single piece of stainless steel. The first side member 11a and second side member 11b are substantially bilaterally symmetrical with respect to each other and include respective angled handle elements 12a and 12b with proximal and distal ends and respective substantially straight, elongated blades 13a and 13b with proximal and distal ends. In the preferred embodiment of the invention, the blades 13a and 13b are 60-70 mm in length. The angled handle elements 12a and 12b, which together constitute a handle 12 and the elongated blades 13a and 13b are fabricated such that the proximal ends of the blades 13a and 13b extend from the distal ends of the respective angled handle elements 12a and 12b at the same one hundred fifteen degree angle. This angle allows the speculum blades 13a and 13b to be inserted into either of the patient's nasal cavities without the handle 12 coming into contact with the patient's mouth and teeth. Further, each of the angled handle elements 12a and 12b are fabricated such that an angle of between one hundred thirty and one hundred forty degrees is formed about half way between their distal and proximal ends. This angle allows a surgeon to easily grasp the speculum handle 12 and manipulate the speculum within the nasal cavity during the course of a procedure. Hereinafter, the surfaces of the endonasal speculum 10 will be described according to the orientation of the speculum as it appears in FIG. 1A. FIG. 1A shows two horizontal axis 18a and 18b and a vertical axis is shown running across FIG. 1A and a vertical axis 18c.

Continuing to refer to FIG. 1A, the elongated blades 13a and 13b are fabricated to have a rounded shape in cross sectional profile for substantially their entire length with the exception of 17 mm of their length at the distal ends of the blades 13a and 13b. The rounded shape of the elongated blades is selected to conform to the shape of the nostril which eases the trauma on the nasal cavity during an operation. Further, the outside surfaces of both elongated blades 13a and 13b include closely spaced ridges that are oriented at right angles to the horizontal axis 18a of the elongated blades. These ridges act to prevent slippage between the inside of the nasal cavity and the outside surface of the speculum during a procedure. At the point 17 mm from the distal ends of the blades 13a and 13b, the cross sectional profile of each blade gradually transitions from a rounded profile to be linear in profile in cross section such that the distal 7 or 8 mm of the elongated blades 13a and 13b are both linear in cross sectional profile. Further with respect to the vertical orientation of the blades 13a and 13b, in one embodiment of the invention, the proximal ends of each elongated blade 13a and 13b are oriented along the vertical axis 18c and the orientation of the upper edges of the elongated blades 13a and 13b gradually transitions to be "open" (trapezoidal-up) with respect to the lower edges of the elongated blades 13a and 13b at a specified up angle to the vertical axis 18c at the distal ends of the blades 13a and 13b. This angled orientation of the distal ends of the blades 13a and 13b with respect to the vertical axis 18c will now be described in more detail below with reference to FIGS. 1B, 1C and 1D.

FIG. 1B is an illustration of the orientation of the proximal ends of the elongated blades 13a and 13b with respect to the plane of the vertical axis 18C. The top edges 19a and 19b and bottom edges 19c and 19d of each elongated blade 13a and 13b are aligned in the plane of the vertical axis 18c. This orientation is desirable at this location of the blades to conform generally to the anatomy of the nasal cavity and to begin to transition to the distal blade trapezoidal design described further below. Moving away from the proximal ends of the elongated blades 13a and 13b along the horizontal axis 18a, the orientation of the blades gradually change with respect to the plane of the vertical axis 18C change as illustrated with reference to FIG. 1C below.

Figure 1C:
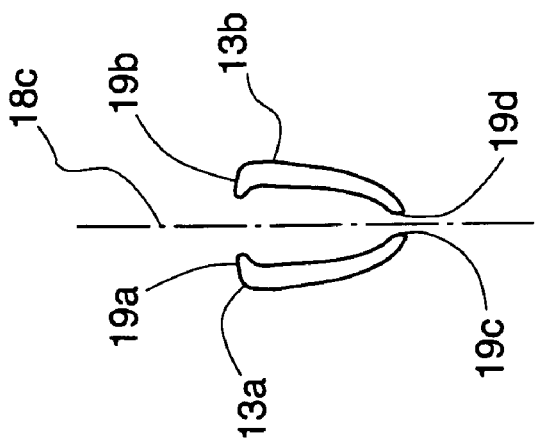
FIG. 1C is a cross sectional view of the middle portion of the speculum blades.

FIG. 1C shows that at a mid-point along the length of the blades 13a and 13b, the upper edges 19a and 19b of the respective elongated blades 13a and 13b have transitioned away from the vertical axis 19C while the bottom edges 19c and 19d have not changed position with respect to the plane of the axis 18C. In this case, a line drawn from the bottom edges 19c and 19d to the respective upper edges 19a and 19b of the elongated blades 13a and 13b defines a particular angle with the vertical axis 18C. Moving away from the mid-points of the elongated blades 13a and 13b along the horizontal axis 18A towards the distal ends of the two blades, the angles defined by the orientation of the blades with the axis 18C become larger as is shown below with reference to FIG. 1D.

FIG. 1D shows the orientation of the elongated blades 13a and 13b at their distal ends. As shown in FIG. 1, the distal ends are linear in cross section and in the preferred embodiment of the invention are each oriented at a specified 15 degree angle with respect to the vertical axis 18C, but the specified angle could be more or less than 15 degrees. More specifically, in a trapezoidal-up embodiment of the speculum the distance between the upper edges 19a and 19b of the respective elongated blades 13a and 13b while the speculum 10 is in the closed position is 9 mm+/−1 mm and the distance between the lower edges 19c and 19d of the respective elongated blades 13a and 13b while the speculum 10 is in the closed position is 5 mm+/−0.5 mm. The previously mentioned 5 degree flaring at the distal ends of each blades 13a and 13b slightly spreads the lower edges 19c and 19d apart from one another when the speculum 10 is in the closed position. As can be seen in FIG. 1D, the orientation of the distal ends of the blades 13a and 13b with respect to the vertical axis 18C describes a trapezoidal shape and so this particular distal blade end configuration is referred to as a trapezoidal "up" configuration. Although the particular embodiment of the speculum described above with reference to FIGS. 1B-1D is that of a speculum fabricated so that its distal ends are at a particular angle that opens "upwards", in another embodiment of the speculum the distal ends are at an angle the opens "downwards" or they are in a trapezoidal "down" configuration. The embodiment of the endonasal speculum fabricated with blades in the trapezoidal "up" configuration is employed for procedures in which the target area extends into the suprasellar region as this blade configuration results in greater visibility and access into this region. The embodiment of the endonasal speculum fabricated with blades in the trapezoidal "down" configuration is employed for procedures in which the target area extends into the infrasellar (below the sella) region as this blade configuration results in greater visibility and access into this region.

Referring again to FIG. 1A, the first and second side members 11a and 11b are attached to each other 5 mm from their proximal ends by a pivot element 16. The pivot element 16 in this case is a three element butt type hinge, but can be any type of hinge that permits the speculum to be opened and closed through a required range of motion. In the preferred embodiment, the pivot element 16 is practically positioned on the speculum to only permit a specific range of motion at the distal ends of the elongated blades 13a and 13b. The opening of the hinged speculum side members 11a and 11b is controlled by a variable dilation control element 17 which is composed of a threaded rod 17b to which is attached at its proximate end a handle 17a. The distal end of the threaded rod 17b butts up against the inner surface of the first side member 11a and passes through a threaded thru hole 17c in side member 11b. In operation, the handle 17c of the dilation control element 17 is rotated clock-wise to cause the threaded rod 17b to press against the inner surface of the first side member 11a thereby causing the first side member 11a to move away from the second side member 11b which results in the speculum blades 13a and 13b opening. Although in the preferred embodiment the dilation control element 17 is described as being composed of a threaded rod and attached handle, it should be understood that other dilation control arrangements can be employed in the speculum 10 as well. Finally, the distal ends of the elongated speculum blades 13a and 13b are both flared outwardly with respect to the horizontal axis 18a running the length of the elongated blades at an angle of 5 degrees. The flaring starts 8 to 10 mm from the distal ends of each of the elongated blades 13a and 13b and proceeds in a smooth, gradual arc to the distal ends of each elongated blade such that the total angle of the flare amounts to 5 degrees. This 5 degree distal flare has the effect of positively retaining soft tissue at the target area thereby preventing the tissue from interfering with the procedure.

With continued reference to FIG. 1A, an oval shaped surgical corridor 15 starts at an aperture 14 located on the upper distal surface of the speculum handle 12 and continues through the handle 12 into the elongated blades 13a and 13b along the horizontal axis 18a for substantially the entire length of the blades 13a and 13b. This surgical corridor is used by a surgeon to insert an endoscope and one or two other micro-instruments, for example, through the speculum in order to perform particular procedures such as tumor removal in the sellar, suprasellar or infrasellar regions within the human head. More specifically, the surgical corridor 15 is formed by cylindrically shaped depressions fabricated horizontally to the axis 18 at the distal ends of each of the opposed inner surfaces of the handle elements 12a and 12b. The inner surfaces of the rounded blades 13a and 13b extend smoothly from each of the cylindrically shaped depressions fabricated in the distal ends of the respective handle elements 12a and 12b to complete the formation of the surgical corridor. Also, the distal ends of each of the handle elements 12a and 12b can be slightly flared to accommodate the surgical corridor 15.

Figure 2:
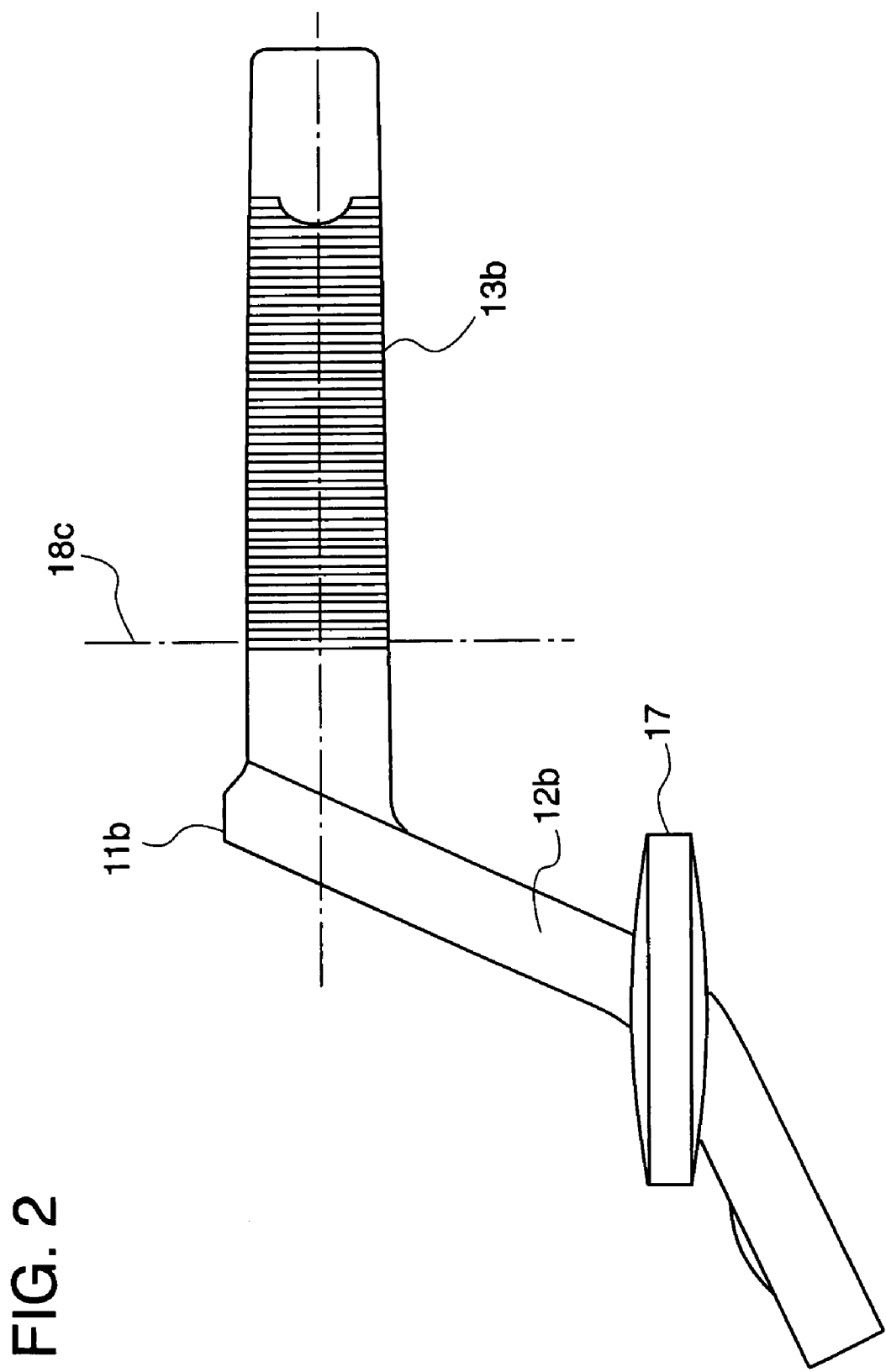
FIG. 2 is a side view of the endonasal speculum.

Referring now to FIG. 2 which is a side view of the endonasal speculum 10 showing relevant dimensions and tolerances needed to fabricate one embodiment of the of the novel endonasal speculum. Shown in FIG. 2 is one side member element 11b which is generally composed of the elongated blade 13b, handle element 12b and dilation control element 17. The side element 11b is 70 mm long with a tolerance of +/−2 mm, it is 11.5 mm wide in the direction of vertical axis 18c with a tolerance of +/−0.5 mm and the blade is 1.5 mm thick with a tolerance of 0.1 mm for substantially its entire length with the exception of the distal 7 to 9 mm portion of the blades. In another embodiment of the endonasal speculum, the elongated blade 13b is 60 mm long with a tolerance of +/−2 mm. The shorter speculum length of 60 mm provides greater instrument maneuverability than the 70 mm speculum because the shorter length is less restrictive, it provides a wider angle of surgical exposure and can be used in children as well as adults. The handle element 12b as described earlier with reference to FIG. 1 is angles at 135 degrees at its midpoint. More specifically, the 135 degree angle is fabricated in the area of the handle element 12b 45 mm+/−2 mm from the distal end and 35 mm+/−2 mm from the proximal end of the handle element 12b. The handle element 12b is generally 7 mm wide along its sides that are in the vertical axis 18c from its proximal end to its distal end and the dilation control element 17 is screwed into a hole located in the area in which the 135 degree angle is fabricated. The location of the dilation control element 17 is selected so that the operator can easily handle the proximal end of the speculum so that it can be maneuvered inside the nasal cavity. The handle 17a referred to earlier in FIG. 1 can be of any dimension that permits the handle to be easily turned by the operator.

Figure 3:
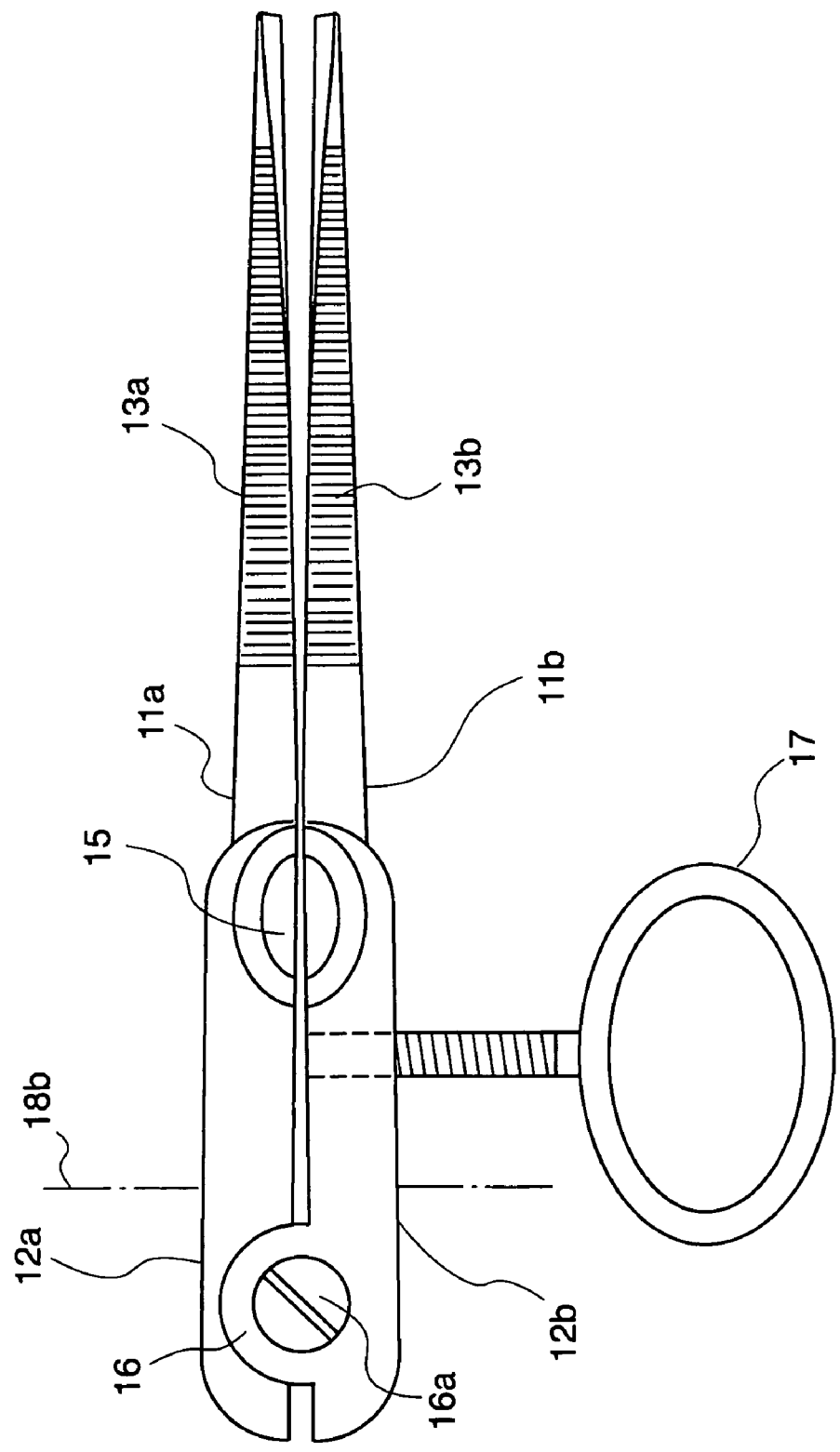
FIG. 3 is a top view of the endonasal speculum.

Referring now to FIG. 3, which is a top view of the endonasal speculum 10 illustrating the two substantially, bilaterally symmetrical speculum side members 11a and 11b each being composed of respective handle elements 12a and 12b and respective elongated blade elements 13a and 13b. Also shown is the top portion of the butt hinge 16 with proximal end of screw 16a and the variable dilation control element 17. Both of the handle elements 12a and 12b are 7 mm wide along the horizontal axis 18b for substantially their entire length with the exception of 20 mm of their distal ends which are not as wide due to the inclusion/formation of the surgical corridor 15. Both of the elongated blades 13a and 13b are 5 mm wide in the dimension that corresponds to the horizontal axis 18b for half of their length at which point their gradually transition to be 1.5 mm wide at their distal ends. The horizontal and vertical dimensions of the aperture 14 that forms the opening for the oval shaped surgical corridor 15, described earlier with reference to FIG. 1, is 13 mm×20 mm as it enters the upper surface of the handle 12. The dimensions of the surgical corridor rapidly narrow in a smooth, tight radius as the corridor passes into the handle 12 and the horizontal and vertical dimensions of the surgical corridor formed by the proximal ends of the elongated blades 13a and 13b are 8 mm×9.5 mm. The top portion of the pivot element 16 is shown extending in a semi-circular manner from the handle element 12b. In this case, the diameter of the semi-circular pivot element is 14 mm and has a radius of 180 degrees, but the diameter of the radius of the pivot element can be smaller or larger without appreciably affecting the effectiveness of the speculum operation. And finally, the handle element 12b is shown as including a variable dilation control element 17 as described earlier with reference to FIG. 1. The handle element 12b includes a threaded thru hole 17c that receives the threaded rod portion of the control element 17. Thru hole diameter is 3 mm and the threaded rod is dimensioned so that it will easily thread into the hole and the control handle 17a can be easily turned by the operator.

Figure 4:
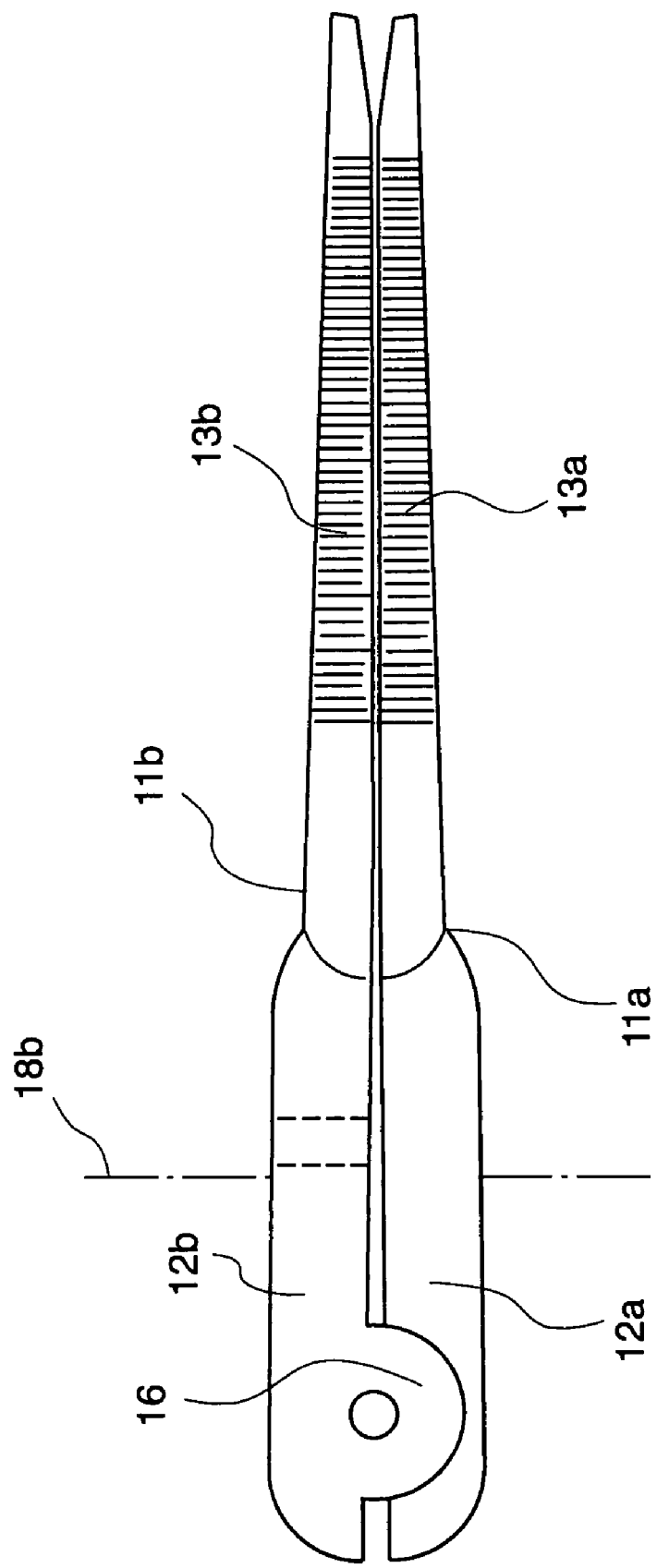
FIG. 4 is a bottom view of the endonasal speculum.

Referring now to FIG. 4, which is a bottom view of the endonasal speculum 10 illustrating the two speculum side members 11a and 11b. This view of the speculum shows substantially the same structure as the top view in FIG. 3 with the exception that the aperture 14 and surgical corridor are not included and the bottom portion of the pivot 16 is shown. Otherwise all of the dimensions remain the same.

The forgoing description, for purposes of explanation, used specific nomenclature and specific dimensions pertaining to particular speculum elements to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

I claim:
1. An endonasal speculum comprising:
first and second substantially bilaterally symmetrical side members having proximal and distal ends joined by a pivot and including variable dilation control;
the first side member including a first handle element and a substantially straight first elongated blade extending at an angle from a distal end of the first handle and the second side member including a second handle element and a substantially straight second elongated blade extending at an angle from a distal end of the second handle element;

a surgical corridor formed by the combination of the distal ends of the first and second handle elements and by substantially the entire length of the first and second elongated blades;

the first and second elongated blades each transitioning from an arcuate cross section at a proximal end to a linear cross section at a distal end, and the distal ends of the first and second elongated blades in cross section are flared away from each other in one of an upward orientation (trapezoidal-up) and downward orientation (trapezoidal-down), wherein both the proximal end cross section and the distal end cross section are oriented perpendicular with respect to the surgical corridor; and the distal ends of each blade are opposed to each other with respect to the perpendicular cross section at a specified angle.

2. The endonasal speculum of claim 1 wherein the variable dilation control includes a threaded rod whose which is disposed within a threaded hole in the second side member.

3. The endonasal speculum of claim 1 wherein the pivot connects the first and second side members at their proximal ends.

4. The endonasal speculum of claim 1 wherein the angle at which the first and second elongated blades extent from the distal ends of the first and second handle elements is between one hundred ten and one hundred fifteen degrees.

5. The flared first and second elongated blades of claim 1 wherein the distal ends of each is flared by no more than five degrees.

6. The endonasal speculum of claim 1 wherein a surface of each of the first and second elongated blades includes closely spaced linear ridges disposed on the surface at right angles to the elongated axis of the blades.

7. The endonasal speculum of claim 1 wherein each of the first and second elongated blades are no less than 60 mm in length and no greater than 70 mm in length.

8. The endonasal speculum of claim 1 is composed of surgical stainless steel.

9. The endonasal speculum of claim 1 wherein the distal ends of each blade are opposed to each other in cross section by no less than 12 degrees and no more than a 15 degree angle in one of an upward (trapezoidal-up) and downward (trapezoidal-down) orientation.

* * * * *